United States Patent
Otts

(10) Patent No.: US 10,850,002 B2
(45) Date of Patent: Dec. 1, 2020

(54) STERILIZATION OF CONTACT LENSES

(71) Applicant: Verily Life Sciences LLC, Mountain View, CA (US)

(72) Inventor: Daniel Otts, Pleasanton, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 300 days.

(21) Appl. No.: 15/697,651

(22) Filed: Sep. 7, 2017

(65) Prior Publication Data

US 2018/0078669 A1     Mar. 22, 2018

Related U.S. Application Data

(60) Provisional application No. 62/397,731, filed on Sep. 21, 2016.

(51) Int. Cl.
*A61L 12/08*     (2006.01)
*B65B 25/00*     (2006.01)
(Continued)

(52) U.S. Cl.
CPC ........... *A61L 12/084* (2013.01); *A61L 12/082* (2013.01); *B65B 25/008* (2013.01); *B65B 55/18* (2013.01); *G02B 1/043* (2013.01); *G02C 7/04* (2013.01)

(58) Field of Classification Search
CPC ... A61L 12/082; A61L 12/084; B65B 25/008; B65B 55/18
See application file for complete search history.

(56) References Cited

U.S. PATENT DOCUMENTS 3,473,886 A    10/1969   Leeds
4,207,287 A     6/1980   Lindquist
(Continued)

FOREIGN PATENT DOCUMENTS

EP      1785153 A2     5/2007

OTHER PUBLICATIONS

International Searching Authority, International Search Report and Written Opinion dated Feb. 26, 2018, issued in connection with International Patent Application No. PCT/US2017/052052.
(Continued)

*Primary Examiner* — Sean E Conley
(74) *Attorney, Agent, or Firm* — McDonnell Boehnen Hulbert & Berghoff LLP

(57) ABSTRACT

An eye-mountable device includes a hydrogel material. By drying the hydrogel material of the eye-mountable device, ethylene oxide may be used to sterilize the eye-mountable device. Such a sterilization method can be employed to sterilize the eye-mountable device when the eye-mountable device includes electronics, sensors, actuated lenses, or other components that may be damaged by heat, pressure, radiation, or other conditions used for sterilization. The eye-mountable device may be stored, dry, within a sealed sterile volume of a packaging material. The packaging material may be permeable to ethylene oxide such that the dried eye-mountable device may be sterilized by ethylene oxide after being sealed within the packaging material. The eye-mountable device could take the form of a contact lens, the form of a device configured to be placed against a sclera of an eye beneath an eyelid of the eye, or could take some other form.

8 Claims, 6 Drawing Sheets

(51) Int. Cl.
  *B65B 55/18* (2006.01)
  *G02B 1/04* (2006.01)
  *G02C 7/04* (2006.01)

(56) References Cited

U.S. PATENT DOCUMENTS

| | | |
|---|---|---|
| 2007/0104611 A1 | 5/2007 | Marmo et al. |
| 2014/0183063 A1* | 7/2014 | Lee ................. B65B 25/008 |
| | | 206/5.1 |
| 2014/0200424 A1 | 7/2014 | Etzkorn et al. |
| 2015/0173474 A1* | 6/2015 | Barrows ............... B65D 81/22 |
| | | 206/5.1 |
| 2017/0097520 A1* | 4/2017 | Lee ..................... G02C 7/04 |

OTHER PUBLICATIONS

Ethylene Oxide (EtO) Sterilization Process, 3pages, http://www.eurotherm.com/eto-sterilization.
Microbiology, pp. 38-77, https://www.fda.gov/downloads/MedicalDevices/.../ucm080968.pdf.

* cited by examiner

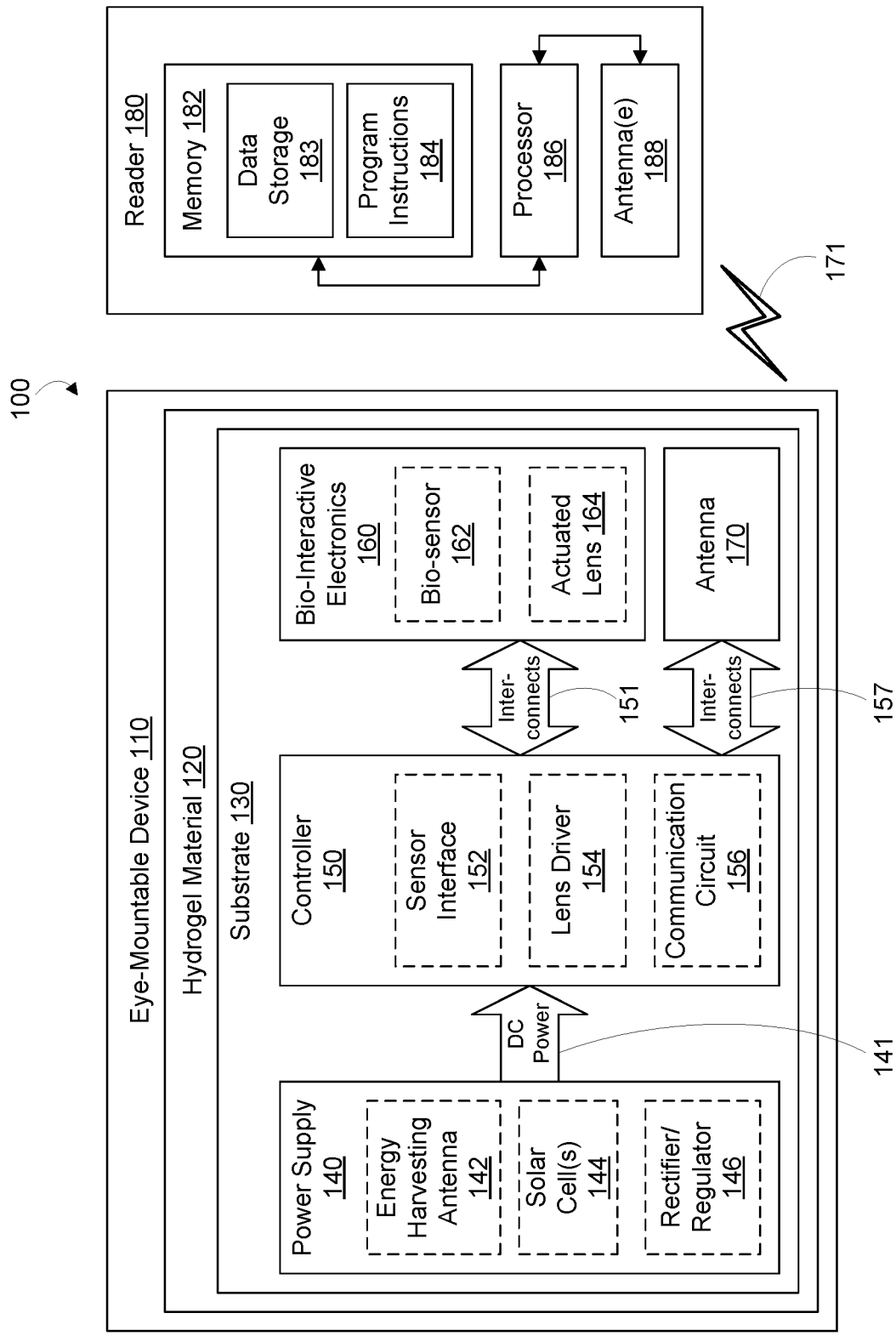

STERILIZATION OF CONTACT LENSES

CROSS-REFERENCE TO RELATED APPLICATION

This application claims the benefit of and incorporates by reference the content of U.S. Provisional Pat. App. No. 62/397,731, filed Sep. 21, 2016.

BACKGROUND

An eye-mountable device may include sensors, actuated lenses, electronics, or other components configured to provide a controllable optical power, to obtain health-related information (e.g., based on at least one analyte detected in tear film of an eye), or to provide some other functionality to a user wearing the eye-mountable device. Such an eye-mountable device may include a sensor apparatus configured to detect at least one analyte (e.g., glucose). Additionally or alternatively, such an eye-mountable device may include an electrowetting lens or other actuated lens to provide a controllable optical power to an eye. In some examples, the eye-mountable device may be in the form of a contact lens that includes a sensor apparatus configured to detect the at least one analyte.

SUMMARY

Some embodiments of the present disclosure provide a method including: (i) drying an eye-mountable device, (ii) placing the eye-mountable device within a gas-permeable enclosure; and (iii) sterilizing the dried eye-mountable device in the gas-permeable enclosure, wherein sterilizing the dried eye-mountable device comprises exposing the dried eye-mountable device to ethylene oxide gas. The eye-mountable device includes electronics and a hydrogel material having a water content, and drying the eye-mountable device includes drying the hydrogel material to remove a portion of the water content.

Some embodiments of the present disclosure provide a system including: (i) an eye-mountable device that includes electronics and a substantially dehydrated hydrogel material; and (ii) packaging material. The eye-mountable device is disposed within an enclosed volume of the packaging material and the enclosed volume of the packaging material is substantially sterile.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 1 is a block diagram of an example system that includes an eye-mountable device in wireless communication with a reader, in accordance with an example embodiment.

DETAILED DESCRIPTION

Figure 2A:
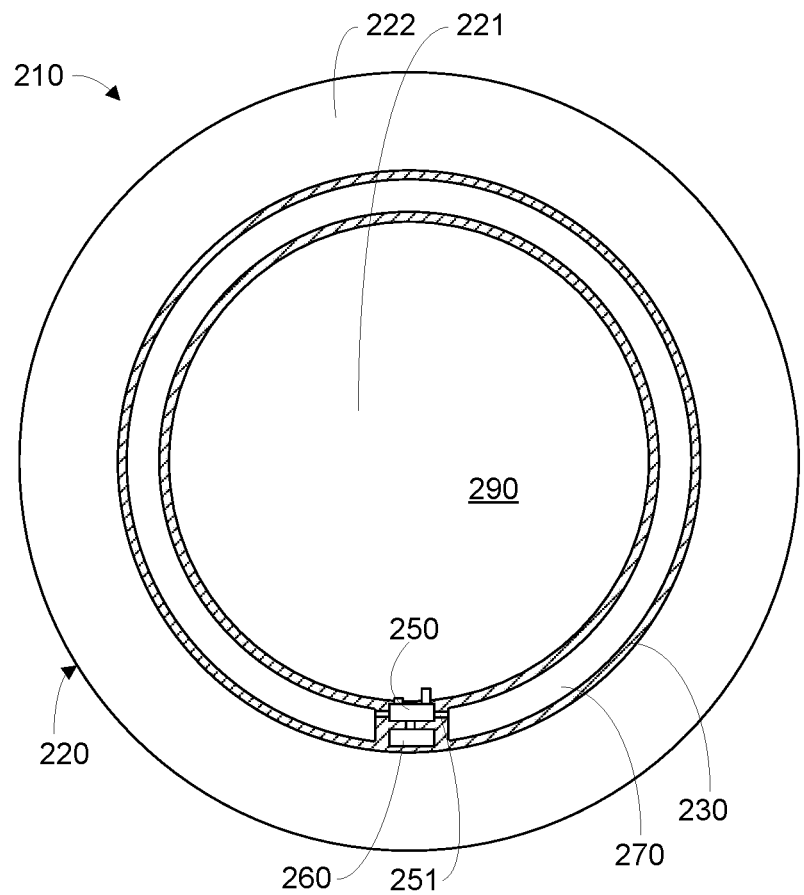
FIG. 2A is a bottom view of an example eye-mountable device, in accordance with an example embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where the operation of a device to measure a hematocrit of blood, or to measure a volume percent of some particulate in some other fluid of interest, is desired.

I. OVERVIEW

An eye-mountable device could facilitate a variety of applications. For example, such an eye-mountable device could be configured to detect a property of an eye (e.g., a concentration of glucose or other analytes in a tear film of the eye), to detect a property of the environment of the eye (e.g., an ambient light intensity), to provide a user input (e.g., by detecting eye blinks), to provide a user output (e.g., by providing a display image to the retina of an eye by emitting patterned light toward the eye), to provide a controllable optical power to the eye (e.g., to facilitate the eye focusing alternatively on near and far objects), or to provide some other applications. Such an eye-mountable device can include a sensor, electronics, an actuated lens, a battery, display element, and/or an antenna embedded in a polymeric material. The electronics can operate the sensor to detect a physical property (e.g., a glucose concentration in tear film), the actuated lens to provide a controllable optical power, the display element to provide a visual indication, the antenna to wirelessly communicate with an external system (e.g., another eye-mountable device, a user interface for specifying the power of the actuated lens), or some other elements of the eye-mountable device to provide some other functionality.

Components (e.g., electronics, sensors, lenses) of such an eye-mountable device could be wholly or partially encapsulated in a polymeric material. The polymeric material could be configured to permit oxygen or other metabolites or other substances to travel through the eye-mountable device (e.g., to permit oxygen to travel from the environment to the cornea of an eye to which such a device is mounted), to provide a lubricated, compliant, or otherwise comfortable surface material to the eye, to permit deformation of the polymeric material (e.g., for comfort, to facilitate contact-mounting of the device to an eye), or to satisfy some other considerations. For example, such a polymeric material could include a hydrogel or some other high-water-content material(s). Such a hydrogel or other polymeric material could be formed to facilitate contact mounting of the eye-mountable device to an eye. For example, the eye mountable device could include electronics or other components wholly or partially embedded within a hydrogel material formed to be mounted over a pupil of the eye and to provide a specified optical power to the eye. In another example, the eye-mountable device could include a hydrogel material formed to be mounted in contact with a sclera of an eye and beneath an eyelid of the eye.

Fabrication and packaging of such an eye-mountable device could include steps for sterilizing the eye-mountable device. Such sterilization could include the application of a specified heat, pressure, radiation flux, chemicals, or other substances, forces, or energies. Ethylene oxide could be applied to an eye-mountable device in order to sterilize the device without exposing the device to damaging levels of heat, pressure, radiation, or other damaging conditions. In order to prevent the applied ethylene oxide from reacting with water in a hydrogel material of the eye-mountable device, the eye-mountable device could be dried before sterilization, e.g., to remove some specified portion of the water content of the hydrogel material. The eye-mountable device could be sealed within a gas-permeable enclosure (e.g., of packaging material used to contain the device) and could be sterilized while within such an enclosure. The eye-mountable device could be dried before being placed in such an enclosure, or, if the enclosure is permeable to water vapor, the eye-mountable device could be dried while within the enclosure. In some examples, such dry packaging and/or storage of the eye-mountable device could prevent deterioration of elements of the device and/or increase a functional shelf-life of the device when stored in such packaging. For example, if the eye-mountable device contains a biological enzyme (e.g., as part of a sensor), storing the device in a dried state may prevent deterioration of the enzyme due to exposure to aqueous solutions (e.g., due to exposure to water stored in an un-dried hydrogel material of the device).

II. EXAMPLE EYE-MOUNTABLE DEVICE

FIG. 1 is a block diagram of a system 100 that includes an eye-mountable device 110 in wireless communication with a reader 180. The exposed regions of the eye-mountable device 110 are made of a polymeric material 120. The polymeric material 120 may be formed to be contact-mounted to a corneal surface of an eye (e.g., over the pupil of an eye), to be mounted beneath an eyelid of an eye (e.g., in contact with a portion of the sclera of the eye that is beneath the eyelid of the eye), or to be mounted to some other portion of an eye. The polymeric material 120 may be composed of a hydrogel material.

A substrate 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting to the cornea of the eye, the polymeric material 120 can have a concave surface configured to adhere ("mount") to a moistened corneal surface (e.g., by capillary forces with a tear-film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

Alternatively, the eye-mountable device 110 could be mountable to a portion or part of an eye other than the cornea. For example, the eye-mountable device 110 could be mountable to the sclera of the eye, e.g., to a portion of the sclera beneath one of the eyelids of the eye. In such an example, the polymeric material 120 can have an ellipsoidal, lunate, or other geometry configured to facilitate placement of the device 110 beneath the eyelid of the eye and in contact with the sclera, to facilitate retention of the device 110 beneath the eyelid, and/or to prevent motion of the device 110 relative to the eye and/or eyelid. Placement of the device 110 beneath an eyelid could provide for improved detection of health properties of a user of the device, e.g., by providing access to tear fluid that is in closer fluid communication with blood of the user's body (e.g., as compared to tear fluid present on the cornea near the pupil of the eye). The polymeric material 120 can have some other shape to facilitate mounting of the device 110 to some other portion of an eye and/or to provide some other functionality.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogel materials and the like. Such hydrogel materials can include a water content disposed within a polymeric or other material of the hydrogel, e.g., to facilitate transport of oxygen and other substances through the hydrogel, to improve comfort, or to provide some other functionality. In some examples, the polymeric material 120 can be a deformable ("non-rigid") material to enhance wearer comfort. In some examples, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. One or more elements of the bio-interactive electronics 160 could be formed on the substrate (e.g., an electrode of an electrochemical sensor, an electrode of an electrowetting actuated lens) or disposed on the substrate (e.g., a window or chamber of an electrowetting actuated lens). Additionally or alternatively, elements of the device 110 could be separate from the substrate 130 and coupled electrically or mechanically to elements on the substrate 130 (e.g., an actuated lens could be disposed proximate to the substrate 130 and connected to components thereon by metallic interconnects).

The substrate 130 can be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some examples, substantially transparent conductive materials (e.g., indium tin oxide) can be patterned on the substrate 130 to form circuitry, electrodes, etc. For example, the antenna 170 can be formed by forming a pattern of gold or another conductive material on the substrate 130 by deposition, photolithography, electroplating, etc. Similarly, interconnects 151, 157 between the controller 150 and the bio-interactive electronics 160, and between the controller 150 and the antenna 170, respectively, can be formed by depositing suitable patterns of conductive materials on the substrate 130. A combination of microfabrication techniques including, without limitation, the use of photoresists, masks, deposition techniques, and/or plating techniques can be employed to pattern materials on the substrate 130.

The substrate 130 can be a relatively rigid material, such as polyethylene terephthalate ("PET") or another material configured to structurally support the circuitry and/or chip-based electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some examples, one or more elements of the bio-interactive electronics 160 (and the substrate 130) can be positioned away from the center of the eye-mountable device 110 and thereby avoid interference with light transmission to the central, light-sensitive region of the eye when the device 110 is mounted over the pupil of the eye. For example, where the eye-mountable device 110 is shaped as a concave-curved disk, the substrate 130 can be embedded around the periphery (e.g., near the outer circumference) of the disk. In some examples, however, the bio-interactive electronics 160 (and the substrate 130) can be positioned in or near the central region of such an eye-mountable device. Additionally or alternatively, the bio-interactive electronics 160 and/or substrate 130 can be substantially transparent to incoming visible light to mitigate interference with light transmission to the eye. Moreover, in some examples, the bio-interactive electronics 160 can include an actuated lens 164 that refracts light from the environment to be received by the eye. The optical power provided by such an actuated lens 164 could be controllable within a range of optical powers such that the retina of a user's eye may receive light, in focus, from objects at different distances from the eye during different periods of time. Thus, elements of the bio-interactive electronics 160 can optionally be positioned in the center of the eye-mountable device so as to provide a useful, controllable optical power to an eye.

In examples, the substrate 130 can be ring-shaped with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius. In other examples, the eye-mountable device 110 could be configured to be mounted beneath an eyelid of an eye or at some other location of an eye; in such examples, the substrate 130 could take a shape other than a ring shape.

In examples, the power supply 140 may be configured to harvest ambient energy to power the controller 150 and the bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to/from the reader 180. That is, the functions of the communication antenna 170 and the energy harvesting antenna 142 can be accomplished with the same physical antenna. The power supply 140 could include a battery (e.g., a sealed lithium ion battery, a zinc battery of a battery having some other chemistry that is activated by exposure to moisture from a tear film). Such a battery could be single-use or rechargeable.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such as bio-sensor 162 in the bio-interactive electronics 160 to obtain input from the biological environment. Additionally or alternatively, the interaction could involve the use of the actuated lens 164 in the bio-interactive electronics 160 to provide a controllable optical power to an eye. The interaction could include other operations, e.g., to provide a visual indication to an eye using a light-emitting pixel array or to detect user inputs in the form of eye motions or eyelid motion.

In one example, the controller 150 includes a sensor interface module 152 that is configured to operate bio-sensor 162. The bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some examples, the sensor interface module 152 can be a potentiostat configured to apply a voltage difference between the working and reference electrodes of the amperometric electrochemical sensor while measuring a current through the working electrode. The bio-sensor 162 can be configured to detect other properties, e.g., to detect motion of an eye, to detect motion of an eyelid, to detect electrical activity of muscles of the eye (e.g., to detect electrical activity of ciliary muscles in the eye in order to determine an amount of optical power to provide, using the actuated lens 164, to the eye), to detect a vergence of the eye relative to an opposite eye, to detect a distance from the eye to a target of the eye, or to detect some other physical variable.

In some instances, a reagent can also be included to sensitize an electrochemical sensor of the bio-sensor 162 to one or more desired analytes. The reagent may be localized proximate the electrochemical sensor so as to selectively react with an analyte in a tear-film. In one example, the reagent may include a biological enzyme. In an example, a layer of glucose oxidase ("GOx") proximal to the working electrode can catalyze glucose oxidation to generate hydrogen peroxide ($H_2O_2$). The hydrogen peroxide can then be electro-oxidized at the working electrode, which releases electrons to the working electrode, resulting in an amperometric current that can be measured through the working electrode. Such a biological enzyme could experience a rate of deterioration over time that is reduced by storing the biological enzyme in a dry or otherwise substantially dehydrated state.

The controller 150 can optionally include a lens driver module 154 for operating an actuated lens 164. The actuated lens 164 can be configured in a variety of ways such that an optical power of the actuated lens 164 is controllable. In some examples, the actuated lens 164 could be an electrowetting lens that includes a lens chamber containing two immiscible fluids (e.g., a droplet of oil disposed on a first surface of the chamber, with the remainder of the chamber occupied by saline or some other polar fluid or solvent). Such an electrowetting lens could include electrodes to which could be applied voltages to control the shape of the interface between the two immiscible fluids (e.g., by controlling a contact angle of one of the fluids relative to an internal surface of the lens 164), thus controlling the optical power provided by the lens 164. In another example, the actuated lens 164 could include one or more layers of liquid crystal. Such a liquid crystal lens could include electrodes to which voltages or currents could be applied to control an effective refractive index, degree of birefringence, or other properties of the one or more layers of liquid crystal, thus controlling the optical power provided by the lens 164. The actuated lens 164 could include microfluidic channels or other microfluidic elements, micropumps, electrowetting pumps, piezoelectric pumps, deformable fluid lens chambers, or other elements to facilitate controlling the optical power provided by the actuated lens 164. The actuated lens 164 could be configured in other ways and/or be operated according to other methods in order to control an amount of optical power provided by the actuated lens 164.

The lens driver module 154 can include, for example, one or more amplifiers, digital-to-analog converters, oscillator, function generators, or other elements to control a voltage or current applied (e.g., via one or more electrodes) to the actuated lens 164 in order to control an optical power or other optical property of the actuated lens 164. In some examples, the lens driver module 154 can include boost circuits, buck circuits, switched capacitors, inductors, voltage doublers, or other circuitry for generating high voltages (e.g., tens of volts) used to operate the actuated lens 164. The lens driver module 154 could include analog-to-digital circuits, sensor drivers, amplifiers, buffers, feedback amplifiers, or other components for determining or sensing an optical power or other properties of the actuated lens 164, e.g., to provide for feedback control of the optical power of the actuated lens 164.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or lens driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical component. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided to components on a chip by rectifier and/or regulator components located on the same chip. That is, the functional blocks in FIG. 1 shown as the power supply block 140 and controller block 150 need not be implemented as physically separated modules. Moreover, one or more of the functional modules described in FIG. 1 can be implemented by separately packaged chips or other components (e.g., a chamber containing immiscible fluids and electrodes of an electrowetting actuated lens) electrically connected to one another.

Additionally or alternatively, the energy harvesting antenna 142 and the communication antenna 170 can be implemented with the same physical antenna. For example, a loop antenna can both harvest incident radiation for power generation and communicate information, e.g., via backscatter radiation.

The reader 180 can be configured to be external to the eye; i.e., is not part of the eye-mountable device 110. Reader 180 can include one or more antennae 188 to send and receive wireless signals 171 to and from the eye-mountable device 110. In some examples, reader 180 can communicate using hardware and/or software operating according to one or more standards, such as, but not limited to, a RFID standard, a Bluetooth standard, a Wi-Fi standard, a Zigbee standard, etc. The reader 180 may be configured to receive and/or log information from the eye-mountable device 110 (e.g., sensor readings measured using the bio-sensor 162) and/or to provide commands to the eye-mountable device 110 (e.g., to provide commands related to a desired optical power that could be provided using the actuated lens 164).

Reader 180 can also include a computing system with a processor 186 in communication with a memory 182. Memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the bio-sensor 162), program settings (e.g., to adjust behavior of the eye-mountable device 110 and/or reader 180), etc. The memory 182 can also include program instructions 184 for execution by the processor 186 to cause the reader 180 to perform operations specified by the instructions 184. For example, the program instructions 184 can cause reader 180 to provide a user interface that allows for retrieving information communicated from the eye-mountable device 110 (e.g., sensor outputs from the bio-sensor 162) and/or for inputting a desired optical power provided by the actuated lens 164 (e.g., to facilitate reading). The reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

In some examples, reader 180 can be a smart phone, digital assistant, wristwatch, control pendant, or other portable computing device with wireless connectivity sufficient to provide the wireless communication link 171. In other examples, reader 180 can be implemented as an antenna module that can be plugged in to a portable computing device; e.g., in scenarios where the communication link 171 operates at carrier frequencies not commonly employed in portable computing devices. In still other examples, the reader 180 can be a special-purpose device configured to be worn relatively near a wearer's eye to allow the wireless communication link 171 to operate with a low power budget. For example, the reader 180 can be integrated in eyeglasses, integrated in a piece of jewelry such as a necklace, earring, etc., integrated in an article of clothing worn near the head, such as a hat, headband, etc., or integrated in a head-mounted display device. In some examples, such a wearable device could include cameras, laser rangefinders, or other components configured to provide information to determine an optical power to provide to eye(s) of a user, via controlling the optical power of the actuated lens 164.

In an example where the eye-mountable device 110 includes an analyte-sensing bio-sensor 162, the system 100 can be operated to monitor an analyte concentration in tear-film on the surface of the eye, beneath an eyelid of the eye, or at some other location on or proximate to the eye. Thus, the eye-mountable device 110 can be configured as a platform for an ophthalmic analyte bio-sensor. The tear-film is an aqueous layer secreted from the lacrimal gland to coat the eye. The tear-film is in contact with the blood supply through capillaries in the structure of the eye and includes many biomarkers found in blood that are analyzed to characterize a person's health condition(s). For example, the tear-film includes glucose, calcium, sodium, cholesterol, potassium, other biomarkers, etc.

The biomarker concentrations in the tear-film can be systematically different than the corresponding concentrations of the biomarkers in the blood, but a relationship between the two concentration levels can be established to map tear-film biomarker concentration values to blood concentration levels. For example, the tear-film concentration of glucose can be established (e.g., empirically determined) to be approximately one tenth the corresponding blood glucose concentration. However, any other ratio relationship and/or a non-ratio relationship may be used. Thus, measuring tear-film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 100 configured as a tear-film analyte monitor, the reader 180 can emit radio frequency radiation 171 that is harvested to power the eye-mountable device 110 via the power supply 140. Radio frequency electrical signals captured by the energy harvesting antenna 142 (and/or the communication antenna 170) are rectified and/or regulated in the rectifier/regulator 146 and a regulated DC supply voltage 141 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the reader 180 (e.g., via the communication circuit 156). The sensor reading can be communicated by, for example, modulating an impedance of the communication antenna 170 such that the modulation in impedance is detected by the reader 180. The modulation in antenna impedance can be detected by, for example, backscatter radiation from the antenna 170.

In some examples, the system 100 can operate to non-continuously ("intermittently") supply energy to the eye-mountable device 110 to power the controller 150 and bio-interactive electronics 160. For example, radio frequency radiation 171 can be supplied to power the eye-mountable device 110 long enough to carry out a tear-film analyte concentration measurement and communicate the results or to control, to modify an optical power provided by the actuated lens 164, and/or to perform some other operations. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the reader 180 can accumulate a set of analyte concentration measurements over time without continuously powering the eye-mountable device 110.

Figure 2B:
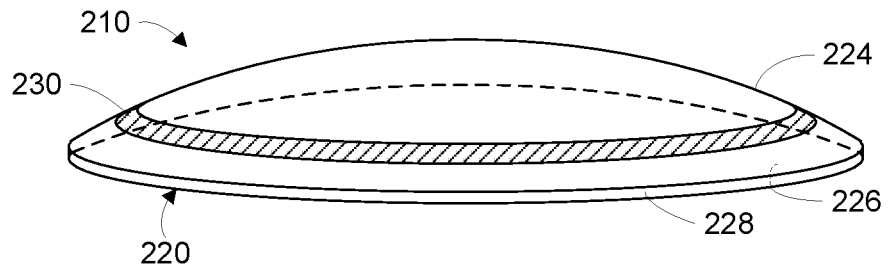
FIG. 2B is a side view of the example eye-mountable device shown in FIG. 2A, in accordance with an example embodiment.

FIG. 2A is a bottom view of an example eye-mountable device 210, in accordance with an example embodiment. FIG. 2B is an aspect view of the example eye-mountable device shown in FIG. 2A, in accordance with an example embodiment. It is noted that relative dimensions in FIGS. 2A and 2B are not necessarily to scale, but have been rendered for purposes of explanation only in describing the arrangement of the example eye-mountable device 210. The eye-mountable device 210 is formed of a polymeric material 220 shaped as a curved disk. In some examples, eye-mountable device 210 can include some or all of the above-mentioned aspects of eye-mountable device 110. In other embodiments, eye-mountable device 110 can further include some or all of the herein-mentioned aspects of eye-mountable device 210. In further embodiments, an eye-mountable device as described herein could have some other shape (e.g., a lunate, ellipsoidal, or other shape) to facilitate placement and retention of the device beneath an eyelid of an eye.

The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("polyHEMA"), silicone hydrogels, silicone elastomers, combinations of these, etc. The polymeric material 220 could be a hydrogel material having a water content. Such a hydrogel material could include a silicone hydrogel and/or silicone elastomer.

The polymeric material 220 could include multiple different materials. For example, electronics of other elements (e.g., substrates, actuated lenses, sensors, batteries) of the eye-mountable device 210 could be encased in a first material of the polymeric material 220. The first material could include a silicone elastomer or other materials configured to provide mechanical protection, stability, or support to the electronics or other elements, to prevent moisture from contacting or condensing into such electronics (e.g., the first material could act as an encapsulating layer), or to provide some other functionality. This first material could then be encased within a hydrogel material (e.g., a silicone hydrogel) that could provide lubrication, a mechanically compliant surface (e.g., to promote comfort when worn on an eye), means for transport of oxygen or other substances through the eye-mountable device 210 (e.g., to facilitate corneal comfort or to allow an analyte of interest to travel through the polymeric material 220 to a sensor of the eye-mountable device 210), or to provide some other functionality.

The polymeric material 220 can be formed with one side having a concave surface 226 suitable to fit over a corneal surface of an eye. The opposite side of the disk can have a convex surface 224 that does not interfere with eyelid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1.4 centimeters, and a thickness of about 0.1 to about 0.5 millimeters. However, the diameter and thickness values are provided for explanatory purposes only. In some examples, the dimensions of the eye-mountable device 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc. can be employed to form the polymeric material 220. While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226. From the bottom view shown in FIG. 2A, an outer periphery 222, near the outer circumference of the curved disk is curved to extend out of the page, whereas the central region 221, near the center of the disk is curved to extend into the page.

A substrate 230 is embedded in the polymeric material 220. The substrate 230 can be embedded to be situated along the outer periphery 222 of the polymeric material 220, away from the central region 221. The substrate 230 does not interfere with vision because it is too close to the eye to be in focus and is positioned away from the central region 221 where incident light is transmitted to the eye-sensing portions of the eye. Moreover, the substrate 230 can be formed of a transparent material to further mitigate effects on visual perception.

The substrate 230 can be shaped as a circular ring (e.g., a disk with a centered hole). The surface of the substrate 230 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors, similar to the discussion of the substrate 130 in connection with FIG. 1 above.

A loop antenna 270, controller 250, and bio-sensor 260 are disposed on the embedded substrate 230. An actuated lens 290 is disposed within the polymeric material 220 in the middle of the substrate 230. The controller 250 can be a chip including logic elements configured to operate the bio-sensor 260, actuated lens 290, and the loop antenna 270. The controller 250 is electrically connected to the loop antenna 270 and bio-sensor 260 by interconnects 251 also situated on the substrate 230. Similarly, the controller 250 is electrically connected to the actuated lens 190 by interconnects 251 that may be located and/or formed on the substrate 230 or that may be configured in some other way. For example, the interconnects between components on the substrate 230 and the actuated lens 290 could include extensions of electrodes that are part of the actuates lens 290, foils disposed on the actuated lens 290 and/or substrate 230, conductive adhesives, or wires connected between pads or other components or features on the substrate 230 and electrodes or other features or components of the actuated lens 290. The interconnects 251, the loop antenna 270, and any conductive electrodes (e.g., for an electrochemical analyte bio-sensor, for an electrowetting actuated lens, for a liquid crystal actuated lens, etc.) can be formed from conductive materials patterned on the substrate 230 by a process for precisely patterning such materials, such as deposition, photolithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, bio-sensor 260 is mounted to a side of the substrate 230 facing the convex surface 224. Where the bio-sensor 260 includes an analyte bio-sensor, for example, mounting such a bio-sensor on the substrate 230 facing the convex surface 224 allows the bio-sensor to sense analyte concentrations in tear-film through a channel 272 (shown in FIGS. 2C and 2D) in the polymeric material 220 to the convex surface 224. In some examples, some electronic components can be mounted on one side of the substrate 230, while other electronic components are mounted to the opposing side, and connections between the two can be made through conductive materials passing through the substrate 230.

In an example, the loop antenna 270 is a layer of conductive material patterned along the flat surface of the substrate 230 to form a flat conductive ring. In some instances, the loop antenna 270 can be formed without making a complete loop. For instances, the loop antenna 270 can have a cutout to allow room for the controller 250 and bio-sensor 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and bio-sensor 260. Interconnects between the ends of such a wound antenna (e.g., the antenna leads) can then be passed through the substrate 230 to the controller 250.

Figure 2D:
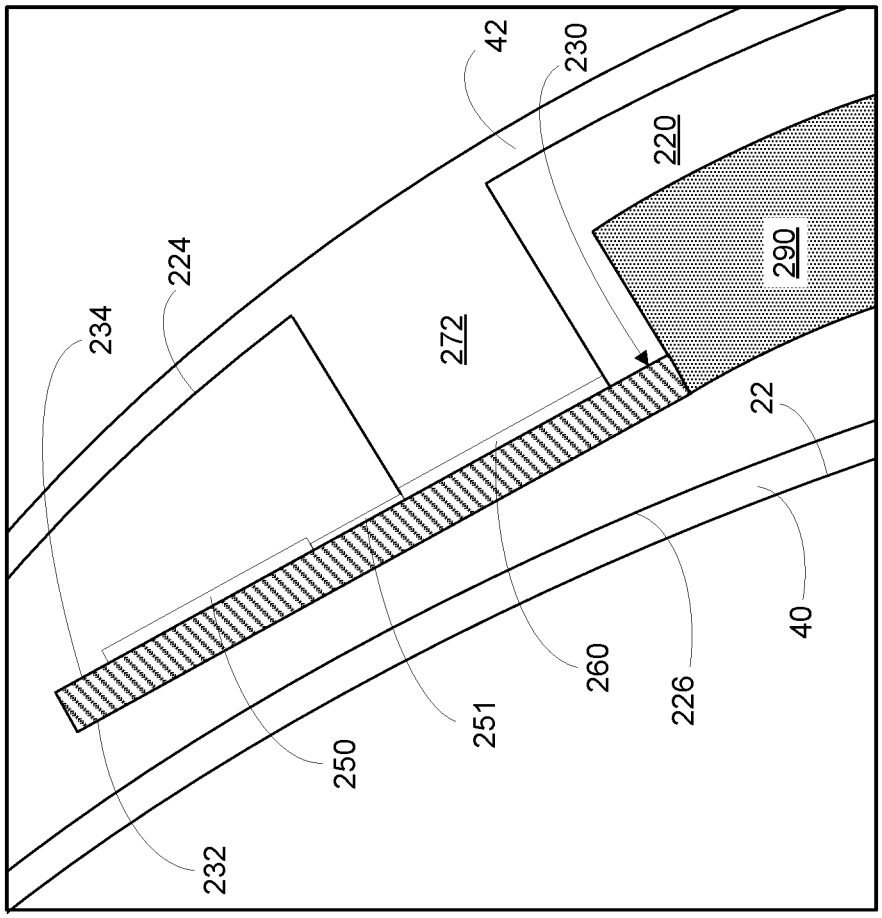
FIG. 2D is a side cross-section view enhanced to show the tear-film layers surrounding the surfaces of the example eye-mountable device when mounted as shown in FIG. 2C, in accordance with an example embodiment.
Figure 2C:
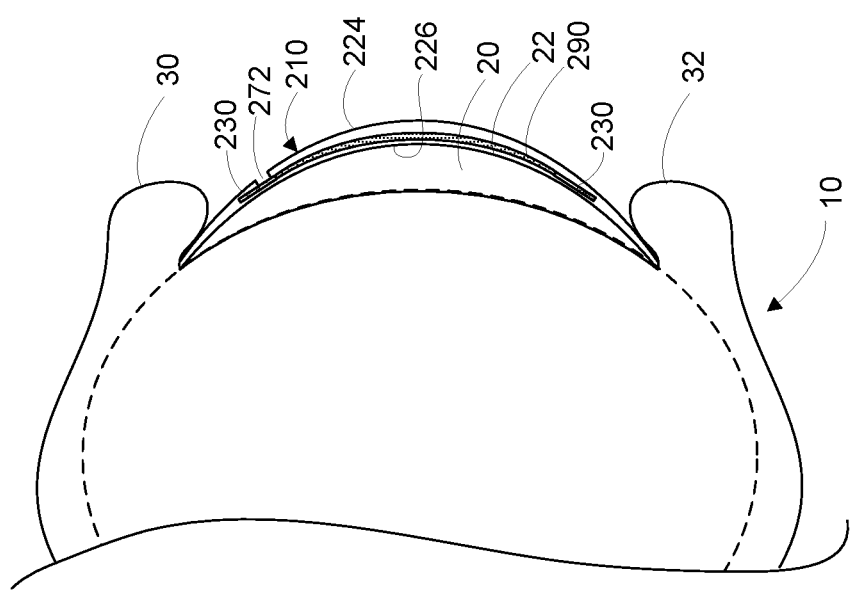
FIG. 2C is a side cross-section view of the example eye-mountable device shown in FIGS. 2A and 2B while mounted to a corneal surface of an eye, in accordance with an example embodiment.

FIG. 2C is a side cross-section view of the example eye-mountable electronic device 210 while mounted to a corneal surface 22 of an eye 10, in accordance with an example embodiment. FIG. 2D is a close-in side cross-section view enhanced to show the tear-film layers 40, 42 surrounding the exposed surfaces 224, 226 of the example eye-mountable device 210, in accordance with an example embodiment. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear-film layers 40, 42 can each be about 10 micrometers, although this ratio may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The curvature of the eye 10, the geometry and optical properties of the eye-mounted device 210, or other factors may affect the focusing and/or refraction of such light received by the eye 10. The actuated lens 290 is disposed over the pupil of the eye 10 such that controlling the optical power of the actuated lens 290 can facilitate control of the distance at which objects in the environment of the eye may be viewed in-focus by the eye 10 (e.g., to facilitate reading).

The motion of the eyelids 30, 32 distributes a tear-film across the exposed corneal surface 22 of the eye 10. The tear-film is an aqueous solution secreted by the lacrimal gland to protect and lubricate the eye 10. When the eye-mountable device 210 is mounted in the eye 10, the tear-film may coat both the concave and convex surfaces 224, 226 with an inner layer 40 (along the concave surface 226) and an outer layer 42 (along the convex layer 224). The tear-film layers 40, 42 can be about 10 micrometers in thickness and together account for about 10 microliters.

The tear-film layers 40, 42 are distributed across the corneal surface 22 and/or the convex surface 224 by motion of the eyelids 30, 32. For example, the eyelids 30, 32 raise and lower, respectively, to spread a small volume of tear-film across the corneal surface 22 and/or the convex surface 224 of the eye-mountable device 210. The tear-film layer 40 on the corneal surface 22 also facilitates mounting the eye-mountable device 210 by capillary forces between the concave surface 226 and the corneal surface 22. In some examples, the eye-mountable device 210 can also be held over the eye in part by capillary forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the convex surface 224. As described above, the substrate 230 may be a flattened ring with an inward-facing surface 232 (facing concave surface 226 of the polymeric material 220) and an outward-facing surface 234 (facing convex surface 224). The substrate 230 can have electronic components and/or patterned conductive materials mounted to either or both mounting surfaces 232, 234. As shown in FIG. 2D, the bio-sensor 260, controller 250, and conductive interconnect 251 are mounted on the outward-facing surface 234 such that the bio-sensor 260 is facing convex surface 224.

The polymer layer defining the anterior side of the eye-mountable device 210 of the eye—may be greater than 50 micrometers thick, whereas the polymer layer defining the posterior side of the eye-mountable device 210 may be less than 150 micrometers. Thus, the bio-sensor 260 may be at least 50 micrometers away from the convex surface 224 and may be a greater distance away from the concave surface 226. However, in other examples, the bio-sensor 260 may be mounted on the inward-facing surface 232 of the substrate 230 such that the bio-sensor 260 are facing concave surface 226. The bio-sensor 260 could also be positioned closer to the concave surface 226 than the convex surface 224. With this arrangement shown in FIGS. 2C and 2D, the bio-sensor 260 can receive analyte concentrations in the tear-film layer 42 through the channel 272.

III. EXAMPLE PACKAGING FOR AN EYE-MOUNTABLE DEVICE

An eye-mountable device may be stored in a package or other enclosure prior to use. Such packaging may maintain the eye-mountable device in a sterile environment until the device is ready for use. Such packaging may also prevent a dried eye-mountable device from being exposed to moisture and/or water vapor, e.g., to prevent deterioration and/or to reduce a rate of deterioration of a biological enzyme (e.g., of a biosensor) or other components of the eye-mountable device. Such packaging may be configured to facilitate the performance of fabrication, sterilization, or other processing steps of or related to the eye-mountable device when the eye-mountable device is sealed within or otherwise location within such a package or other enclosure.

Figure 3A:
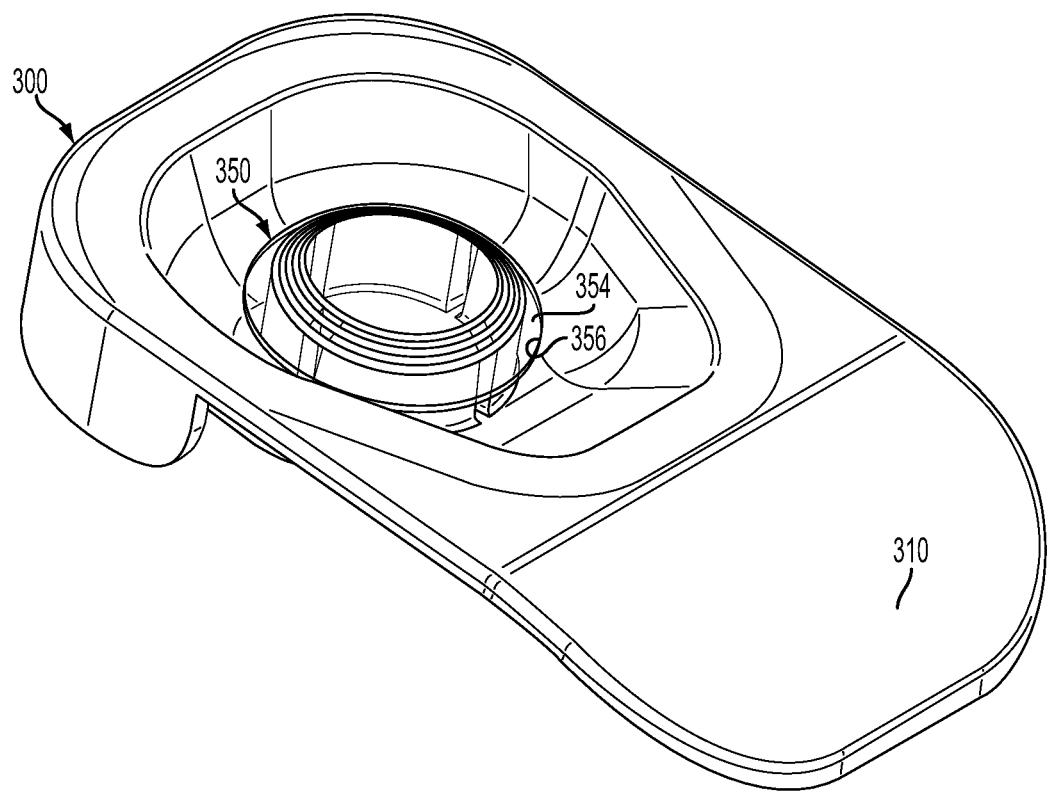
FIG. 3A illustrates a portion of a package that includes an eye-mountable device, in accordance with an example embodiment.
Figure 3B:
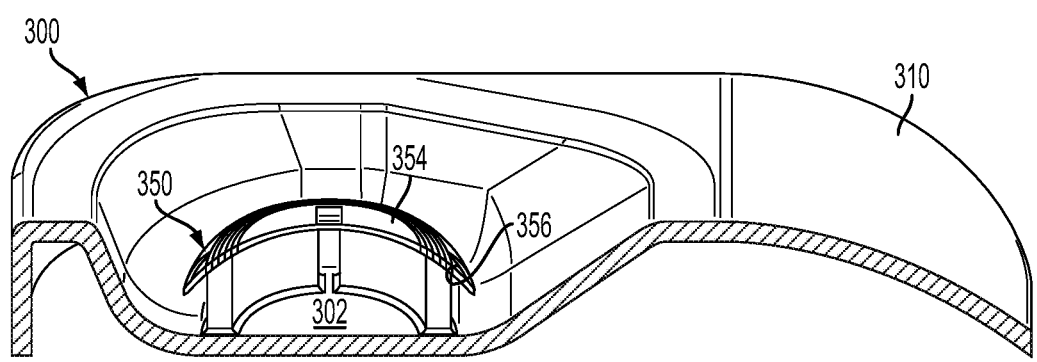
FIG. 3B illustrates a cross section of a side view of the portion illustrated in FIG. 3A, in accordance with an example embodiment.

FIG. 3A illustrates a portion of a package including a container 300, a pedestal 302, and an eye-mountable device 350, in accordance with an example embodiment. FIG. 3B illustrates a cross section of a side view of the portion illustrated in FIG. 3A, in accordance with an example embodiment. The container 300 includes a pedestal 302 having a base and walls that extend from the base to support an eye-mountable device 350. The eye-mountable device 350 may, for example, be similar to the eye-mountable devices 110 and 210 described above. In an example, the container 300 may be made of a polymeric material. For instance, the polymer may include polyethylene terephthalate glycol, which is a thermoplastic polymer resin. However, other materials can be used as well. For example, the container 300 may be made of a polyolefin, such as polypropylene, or any other material (resilient or rigid).

Forming the container 300 may involve injection molding or thermoforming or any other manufacturing process(es) appropriate for the material of the container 300. Example manufacturing processes that could be used to form the container 300 may include spinning inserting, implanting, gluing, laminating, hot pressing, rolling into, molding, stamping, lathing, milling, three-dimensional printing, or a combination thereof. In one example, the container 300 and the pedestal 302 are formed separately, and the pedestal 302 is inserted into the cavity of the container 300 where the first end of the pedestal 302 is attached or coupled to the container 300 (e.g., via an adhesive or any other attachment technique). In another example, the container 300 and the pedestal 302 are formed as one component or a single integral item via, for example, injection molding, or any other technique.

The container 300 may include other parts as well. For example, the container 300 includes a handle 310 to facilitate gripping and moving the container 300. The container 300 may also include any other ergonomic components or parts that facilitate handling the container 300, positioning the container 300 in other packages, etc.

Figure 3C:
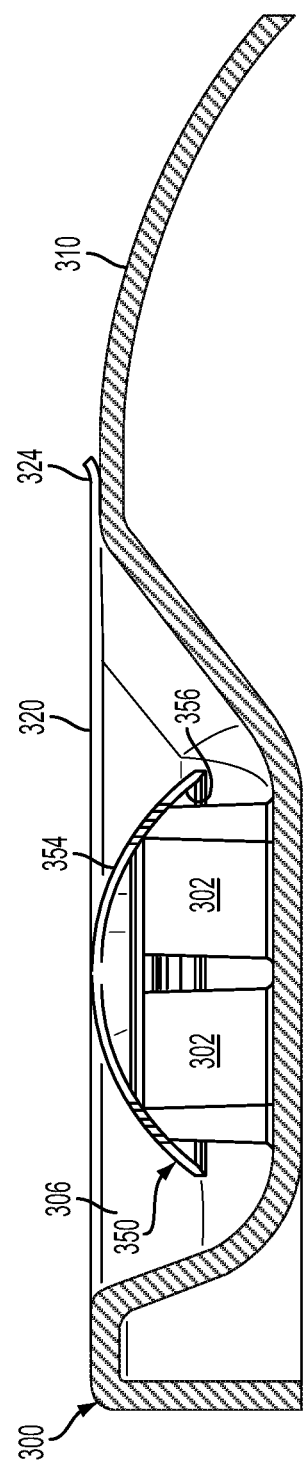
FIG. 3C illustrates a cross section of a side view of the package illustrated in FIGS. 3A and 3B, showing a lidstock, in accordance with an example embodiment.

The cavity inside the container 300 forms a compartment of sufficient size to contain the eye-mountable device 350. FIGS. 3A, 3B, and 3C depict the eye-mountable device 350 having an anterior convex side 354 (similar to the convex surface 224 of the eye-mountable device 210) and a posterior concave side 356 (similar to the concave surface 226 of the eye-mountable device 210) opposite the anterior convex side 354. The eye-mountable device 350 is mounted on the pedestal 302 such that the posterior concave side 354 contacts the second end of the pedestal 302 and the eye-mountable device 350 is elevated from the base of the container 300. The material of the pedestal 302 can be compatible with the material of the eye-mountable device 502, for example, to prevent scratching or abrasion between the pedestal 302 and the posterior concave surface 356.

FIG. 3C illustrates a cross section of a side view of the package showing a lidstock 320, in accordance with an example embodiment. FIG. 3C depicts the lidstock 320 configured to seal an opening 306 of the container 300 to form a gas-permeable enclosure containing the eye-mountable device 350. The enclosure being gas-permeable could include the lidstock 320 being composed of a porous membrane or other material that is permeable to gas (e.g., to ethylene oxide gas) and the container 300 being substantially impermeable to gas. Additionally or alternatively, the container 300 could be gas permeable.

A gas-permeable porous membrane of the lidstock 320 could be configured to allow ethylene oxide gas to permeate through the porous membrane (e.g., to facilitate sterilization of the eye-mountable device 350 by the ethylene oxide gas) while preventing liquids (e.g., liquid water) from permeating through the porous membrane. Such a porous membrane could be composed of a plurality of high-density polyethylene fibers. For example, the lidstock 320 may be made of a Tyvek® material that contains high-density polyethylene fibers. The lidstock 320 may be made of a porous membrane configured to allow gas having molecules of a predetermined size to pass through the lidstock 320. The package described and illustrated in FIGS. 3A, 3B, and 3C can thus be a dry (i.e., substantially free of liquids) and/or substantially dehydrated (e.g., containing less than 5% of a prior water content), microbial-resistant, sterile enclosure suitable for containing and storing the eye-mountable device 350 in a dry (and/or substantially dehydrated), sterile state.

The lidstock 320 may be heat-sealed on the opening 306. The lidstock 320 may be coated with a heat-sealable adhesive material. Pressure can be applied to the lidstock 320 at a given temperature to affix the lidstock 320 to a rim of the opening 306. The opening 306 may have a flanged shape so as to facilitate sealing the opening 306 using the lidstock 320.

The lidstock 320 contacts and presses on the anterior convex side 354 of the eye-mountable device 350, and thus securely holds the eye-mountable device 350 against the pedestal 302 as shown in FIG. 3C. In this way, the position of the eye-mountable device 350 within the enclosure formed from the container 300 and the lidstock 320 is maintained in a manner that does not distort the shape of the eye-mountable device 350. Although FIG. 3C shows the lidstock 320 contacting the anterior convex side 354 of the eye-mountable device 350, in some examples, as described above, there may be a distance between the lidstock 350 and the anterior convex side 354, where the distance is sufficiently small so as to not let the eye-mountable device 350 move or fall off from atop the pedestal 302.

In an example, the lidstock 320 may include a tab portion 324. The tab portion 324 facilitates removing the lidstock 320 by a user when the use is ready to use the eye-mountable device 350. The tab portion 324 may be equipped with any feature that increases friction between user's fingers and the tab portion 324 to ensure a secure grip by the user during the process of opening the package (i.e., removing the lidstock 320).

The lidstock 320 could further include a vapor barrier to prevent the passage of water vapor or other gases into the enclosure containing the eye-mountable device 350. Such a vapor barrier could be applied after sterilizing and/or drying the eye-mountable device 350 such that ethylene oxide, water vapor, or other gases may enter and/or exit the enclosure during such sterilization and/or drying. Additionally or alternatively, the packaging, including the container 300 and lidstock 320, could be placed within a vapor barrier, e.g., within a secondary container that is configured to prevent passage of vapor through the secondary container. Placement of the container 300, lidstock 320, and eye-mountable device 350 sealed therein within such a secondary container could prevent moisture (e.g., water vapor) from the environment of the secondarily container from interacting with the container 300, lidstock 320, and/or eye-mountable device 350.

The vapor barrier could be provided to prevent water vapor from entering the enclosure and wetting or otherwise interacting with the eye-mountable device 350 (e.g., to prevent the hydrogel material of the device 350 from absorbing water vapor from the environment). Prevention of water vapor (or other gases) from interacting with the eye-mountable device 350 could increase a shelf-life of the stored eye-mountable device 350, e.g., by reducing a rate of deterioration of a biological enzyme of the device 350 when such an enzyme is exposed to an aqueous fluid. A vapor barrier of the lidstock 320 or of some other object (e.g., of a secondary container) could include a metal foil. Such a foil could be adhered to a porous membrane or other elements of the lidstock 320 and/or the container 300 by an adhesive or by some other means.

As described above, the eye-mountable device 350 is dried before being sterilized by exposure to ethylene oxide gas. Before the eye-mountable device 350 is mounted to the eye of a user, the hydrogel material (or other elements) of the eye-mountable device 350 may be rehydrated by applying an aqueous solution (e.g., a saline solution) to the eye-mountable device 350 for a period of time (e.g., more than approximately 30 minutes) before use. In some embodiments, the aqueous solution may be a multi-purpose contact lens solution, or a catalytically decomposable hydrogen peroxide disinfecting solution.

In some examples, the eye-mountable device 350 may include at least one sensor configured to measure concentration of a given analyte. The eye-mountable device 350 may include a reagent (e.g., an enzyme such as glucose oxidase) localized proximate an electrochemical sensor so as to selectively react with an analyte in a tear-film. Before such an eye-mountable device is mounted the eye of the user, the sensor may be calibrated so as to ensure accuracy of measurements captured by the sensor. The packaging depicted in FIGS. 3A, 3B, and 3C is configured to facilitate such calibration.

When the package is received by a user, the lidstock 320 may be removed (e.g., by pulling the tab portion 324), and a calibration solution with a known concentration of an analyte of interest may be injected or poured in the container 300. The calibration solution could be, for example, an artificial solution with a composition that is similar to that of a normal tear-film. Thus, the eye-mountable device 350 can be fully immersed in the calibration solution as the calibration solution contacts both the anterior convex side 354 as well as the posterior concave side 356.

The eye-mountable device 350 can be exposed to the calibration solution with the known analyte concentration and a sensor reading is obtained while the eye-mountable device 350 remains exposed. The sensor result (e.g., the amperometric current) divided by the concentration of the analyte can be set as the sensitivity of the eye-mountable device 350, and a linear relationship can be established with the sensitivity as the slope to relate future and/or past sensor results to analyte concentrations.

In some examples, the calibration process is initiated by signaling the external reader (e.g., the reader 180) to indicate the eye-mountable device 350 is exposed to the calibration solution with known analyte concentration. Such a signal can be generated by, for example, a user input. The external reader can emit radio frequency radiation to be harvested by the eye-mountable device 350 to power the sensor and control electronics to perform a sensor reading and communicate the result back to the external reader. The external reader can extract from the reading, a calibration value relating the sensor readings to analyte concentrations. That is, the calibration value can be a slope and/or intercept characterizing a linear relationship relating amperometric currents measured with the electrochemical sensor and analyte concentrations. Subsequent sensor readings when the eye-mountable device 350 is removed an mounted to an eye of the user can then be interpreted according to the calibrated relationship set by the sensor readings obtained with the calibration solution.

IV. EXAMPLE METHODS

Figure 4:
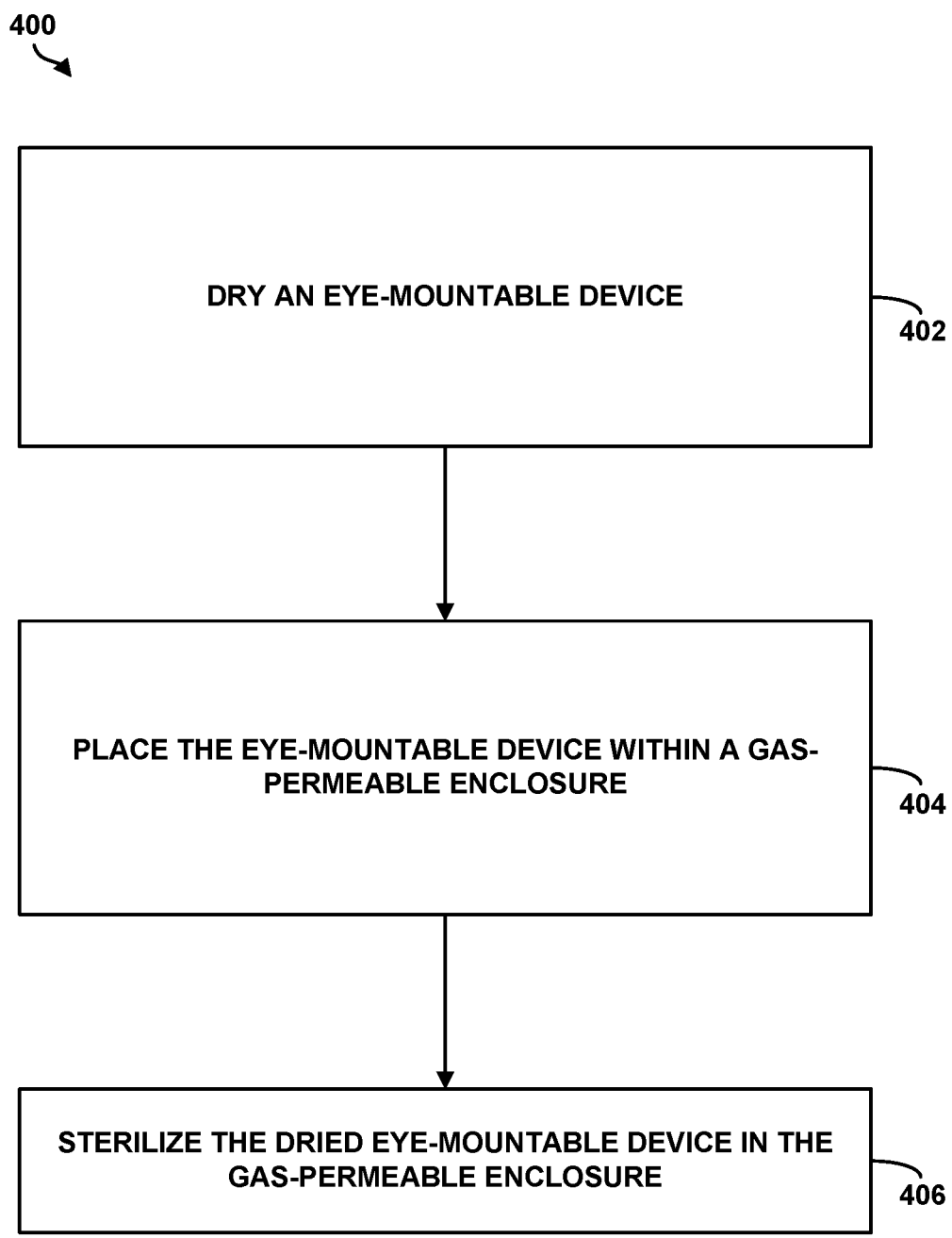
FIG. 4 is a flowchart of a method.

FIG. 4 is a flowchart of a method 400 for sterilizing an eye-mountable device, in accordance with an example embodiment. The eye-mountable device includes electronics (e.g., a controller, a sensor, an antenna, an actuatable lens) and a hydrogel material having a water content. The hydrogel material could be formed to facilitate contact-mounting of the eye-mountable device to an eye and/or mounting of the eye-mountable device beneath an eyelid of an eye. Further, the hydrogel material could be formed to at least partially encapsulate the controller, sensor, antenna, actuatable lens, or other elements of the eye-mountable device. The method 400 may include one or more operations, functions, or actions as illustrated by one or more of blocks 402-406. Although the blocks are illustrated in a sequential order, these blocks may in some instances be performed in parallel, and/or in a different order than those described herein. For example, the eye-mountable device may be dried before or after being placed within a gas-permeable enclosure. Also, the various blocks may be combined into fewer blocks, divided into additional blocks, and/or removed based upon the desired implementation.

At block 402, the method 400 includes drying the eye-mountable device. This could include applying a specified reduced pressure (e.g., a pressure that is lower than ambient pressure by a specified amount), a specified temperature, or some other specified conditions to the eye-mountable device. In some examples, the eye-mountable device could be exposed to air having a humidity below a specified level. Drying the eye-mountable device (402) could include removing at least a specified amount of a water content of the hydrogel material of the eye-mountable device. For example, drying the eye-mountable device (402) could include removing more than 95 percent of the water content of the hydrogel material. As a result of the drying, the hydrogel material could become substantially dehydrated (e.g., the hydrogel material could lose more than 95% of an original water content of the hydrogel material). Removing a specified amount of the water content of the hydrogel material could include applying a specified set of conditions for a specified amount of time and/or detecting a water content of the hydrogel material over time and adjusting properties of the drying (e.g., adjusting a duration of application of a reduced pressure) based on the detected water content. Drying the eye-mountable device (402) could additionally include drying a reagent of the eye-mountable device (e.g., drying a biological enzyme or other reagent of an analyte sensor or other element(s) of the eye-mountable device).

At block 404, the method 400 includes placing the eye-mountable device within a gas-permeable enclosure. This could include placing the eye-mountable device within a container and sealing the eye-mountable device within a volume of the container by applying a lidstock or other sealing means to the container. Such a lidstock and/or such a container could be gas-permeable (e.g., could be composed of a porous membrane or other element formed from fibers of high-density polyethylene or some other porous material). In examples where the gas-permeable enclosure is permeable to at least water vapor, the eye-mountable device could be placed within the gas-permeable enclosure before drying the eye-mountable device.

At block 406, the method 400 includes sterilizing the dried eye-mountable device in the gas-permeable enclosure. This could include exposing the gas-permeable enclosure to ethylene oxide gas for a specified period of time. The ethylene oxide gas could be composed entirely of ethylene oxide or could include other components, e.g., carrier gases, noble gases, or other substances. Exposing the gas-permeable enclosure to ethylene oxide gas could include exposing the gas-permeable enclosure to ethylene oxide gas at a specified temperature, temperature, or other specified conditions. Sterilizing the dried eye-mountable device in the gas-permeable enclosure (406) could include pre-treating the dried eye-mountable device (e.g., by exposing the dried eye-mountable device to a vacuum to remove volatiles from the hydrogel material or other elements of the eye-mountable device) and or post-treating the dried eye-mountable device (e.g., by exposing the dried eye-mountable device to a vacuum to remove any remaining ethylene oxide gas from the enclosure, the hydrogel material, or other elements of the eye-mountable device).

The method 400 may include additional or alternative steps. For example, the method 400 could include adding a vapor barrier (e.g., a metal foil) to the enclosure in order to prevent water vapor or other gases from entering the enclosure and interacting with the eye-mountable device. Additionally or alternatively, the enclosure could be placed and/or sealed within such a vapor barrier (e.g., within a secondary enclosure comprising such a vapor barrier, e.g., a blister pack composed of metal foils or other vapor-impermeable materials). The method 400 could include opening the enclosure and/or removing the eye-mountable device and applying an aqueous solution (e.g., a saline solution, a calibration solution) to rehydrate the hydrogel material or other elements of the eye-mountable device or to facilitate some other process (e.g., a calibration process of a sensor of the eye-mountable device). The method 400 could include other elements.

V. CONCLUSION

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:
1. A system comprising:
   an eye-mountable device, wherein the eye-mountable device comprises electronics and a substantially dehydrated hydrogel material; and
   packaging material, wherein the eye-mountable device is disposed within an enclosed volume of the packaging material, wherein the enclosed volume of the packaging material is substantially sterile, wherein the packaging includes (i) a porous membrane that is permeable to ethylene oxide gas while being non-permeable to liquids, and (ii) a vapor barrier that prevents water vapor from entering the enclosed volume of the packaging material.

2. The system of claim 1, wherein the porous membrane comprises a plurality of fibers, wherein the plurality of fibers comprise high-density polyethylene.

3. The system of claim 1, wherein the eye-mountable device includes a sensor that is operable to measure concentration of an analyte, and wherein the sensor includes a reagent that selectively reacts with the analyte.

4. The system of claim 3, wherein the reagent is dry.

5. The system of claim 4, wherein the reagent comprises an enzyme.

6. The system of claim 1, wherein the vapor barrier comprises a metal foil.

7. The system of claim 1, wherein the wherein the eye-mountable device includes an actuatable lens that is operable to control an optical power of the actuatable lens.

8. The system of claim 7, wherein the actuatable lens comprises an electrowetting lens.

* * * * *